Figure 1:
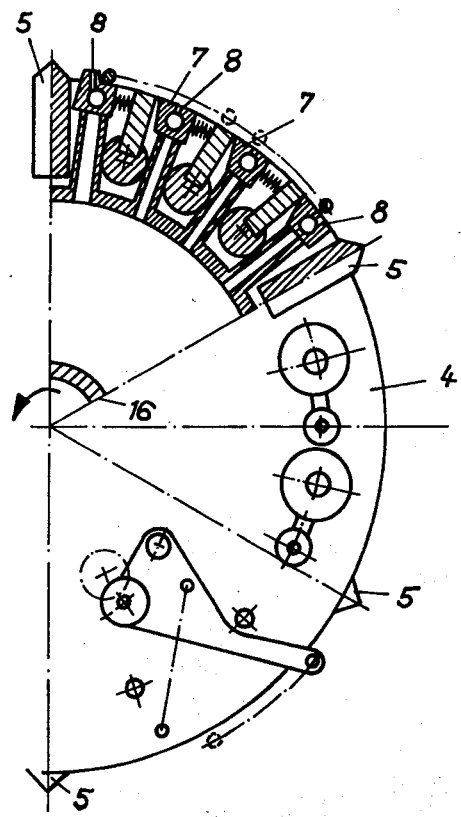

United States Patent [19]

Bouda

[11] 4,272,066
[45] Jun. 9, 1981

[54] APPARATUS FOR PRODUCING COMPRESSES FOR COVERING WOUNDS

[76] Inventor: Horymir J. Bouda, Katleingasse 10, Wien-Mauer, Austria, A-1238

[21] Appl. No.: 940,003

[22] Filed: Sep. 6, 1978

[30] Foreign Application Priority Data

Sep. 9, 1978 [AT] Austria ............................ 6511/78

[51] Int. Cl.³ .......................................... B65H 45/18
[52] U.S. Cl. .................................... 493/418; 493/425
[58] Field of Search ................... 270/61 R, 62, 69, 72, 270/82, 67, 83–85

[56] References Cited

U.S. PATENT DOCUMENTS

| | | | |
|---|---|---|---|
| 2,699,936 | 1/1955 | Dixon | 270/84 |
| 3,640,522 | 2/1972 | Oelmann | 270/72 |
| 3,994,486 | 11/1976 | Nystrand | 270/62 |

*Primary Examiner*—Edgar S. Burr
*Assistant Examiner*—A. Heinz
*Attorney, Agent, or Firm*—Schwartz, Jeffery, Schwaab, Mack, Blumenthal & Koch

[57] ABSTRACT

An apparatus for producing compresses to cover wounds comprises a rotary drum on which a muslin strip having folded-over longitudinal edges is cut and folded crosswise, and a longitudinal folding device mounted after the drum. The drum is designed as a suction roll with cutters distributed over its circumference. The drum jacket has suction rails with extensions connected to a tube leading into the drum and connected to a suction pipe. A counterpiece mounted independently of the drum cooperates with the cutters. The longitudinal folding device has at least a two-arm, preferably a three-arm star shaped collector device which rotates around an axis parallel to the drum axis at the same circumferential speed as the drum itself, and the distance between the arms of the collector device corresponds to the size of the compresses folded on the drum. The folding device has also a collector rake for collecting the compresses from the collector device, and two folding plates are slideably mounted between two folding fingers on two folding tracks. At the end of one folding track the compresses are engaged in a clamping device and at the end of the other folding track a stacking finger stacks the folded compresses.

22 Claims, 22 Drawing Figures

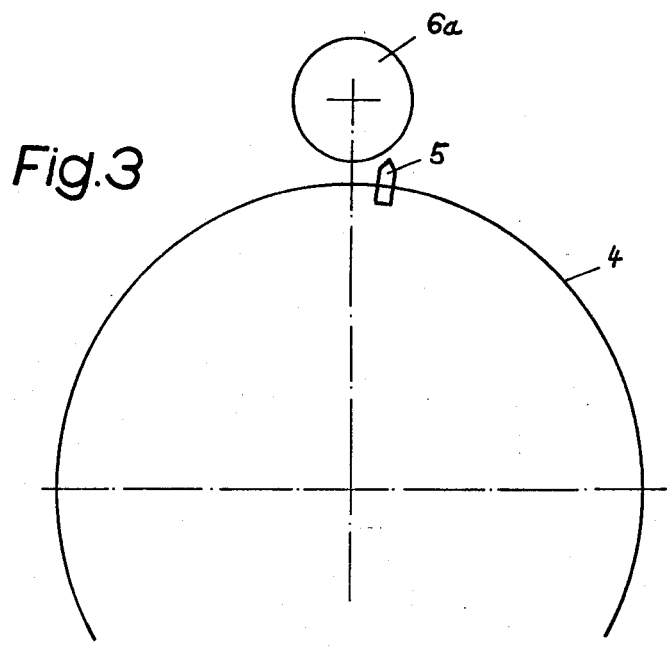
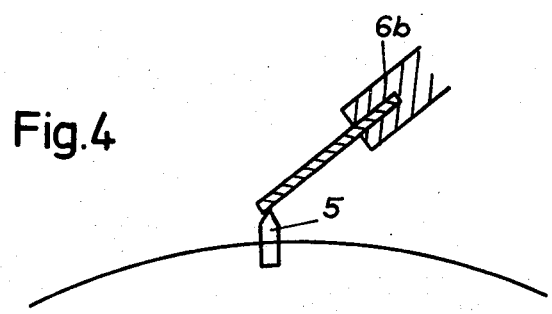

APPARATUS FOR PRODUCING COMPRESSES FOR COVERING WOUNDS

This invention relates to an apparatus for producing compresses for covering wounds and made from strips of muslin fabric which have folded-over longitudinal edges, the apparatus comprising a rotary drum on which the muslin strips are cut and folded crosswise, and a longitudinal folding device mounted after the drum, wherein the drum is designed as a suction roll and presents cutters distributed along its circumference.

In known apparatus of this type the cutters of the drum press against a roll which is fixed in the frame of the drum. In this way the entire machine frame of the apparatus shakes severely with each cut so as to cause a high stress on the frame. Furthermore, when handling wide and thin muslin strips in the known apparatus, they are not severed entirely so that some fibers of the muslin strips extend therefrom. The muslin strip placed on the drum is held thereon by the suction of air through bores provided in the drum jacket which effect can be obtained only with a high suction force. In the known apparatus the cross-folded muslin strip is sucked away from the drum by a cylinder which is at a relatively substantial distance from the drum due to the projecting knives, so that a very high suction effect is necessary in order to lift off the muslin strip. Furthermore, the longitudinal folding device of the known apparatus is suitable for only one type of fold so that the known apparatus can be employed only with certain limitations.

It is an object of the present invention to improve the known apparatus described above. This is obtained according to the invention in that the drum jacket presents suction strips or rails having extensions which are connected to a tube set into the drum and which is in turn connected to a suction line, and that independently of the drum, a counter-piece is provided which cooperates with the cutters. This construction reduces the necessary suction effect considerably and avoids a shaking of the drum.

An additional feature of the invention provides that the cutters are arranged at the periphery of the drum roll. The arrangement is such that the wear of the cutters is very small and even very thin muslin strips can be entirely severed.

The invention provides further that the longitudinal folding device comprises at least a two-arm, and preferably a three-arm or star shaped receiver unit which rotates around an axis that is parallel to the drum axis and at the same circumferential speed as the drum itself, that the distance between the arms of the receiver unit corresponds to the size of the compresses folded on the drum, that the longitudinal folding device further comprises a collector rake for collecting the compresses from the receiver unit and presents two folding plates which are slideable between folding fingers, one such plate being adapted to be slideable into a groove of the receiver unit while the other is arranged to be slideable parallel to the axis of the receiver unit, wherein preferably the longitudinal folding device is slideable relative to the drum and to the axial extension of the receiver surface for the compresses which are collected from the drum. This displacement makes it possible to feed the compresses of the longitudinal folding device in a variable manner whereby several types of folding arrangements are possible.

A preferred embodiment of the invention provides that between the folding fingers two folding tracks are mounted which are disposed at a right angle to each other, in which tracks the folding plates are slideably mounted, wherein the folding track disposed normal to the rotary axis of the collector unit leads into a clamping device, while at the end of the other folding track a stacking finger is mounted which stacks the completely folded compresses in a canal disposed perpendicularly thereto. This construction makes it also possible to fold very thin one-layer muslin compresses.

An additional feature of the invention resides in the fact that the folding track normal to the axis of the collector unit is slideable parallel to this axis. In this way several different positions of the muslin strip to the folding track and thus the production of compresses having a V and VV-fold are possible.

Figure 2:
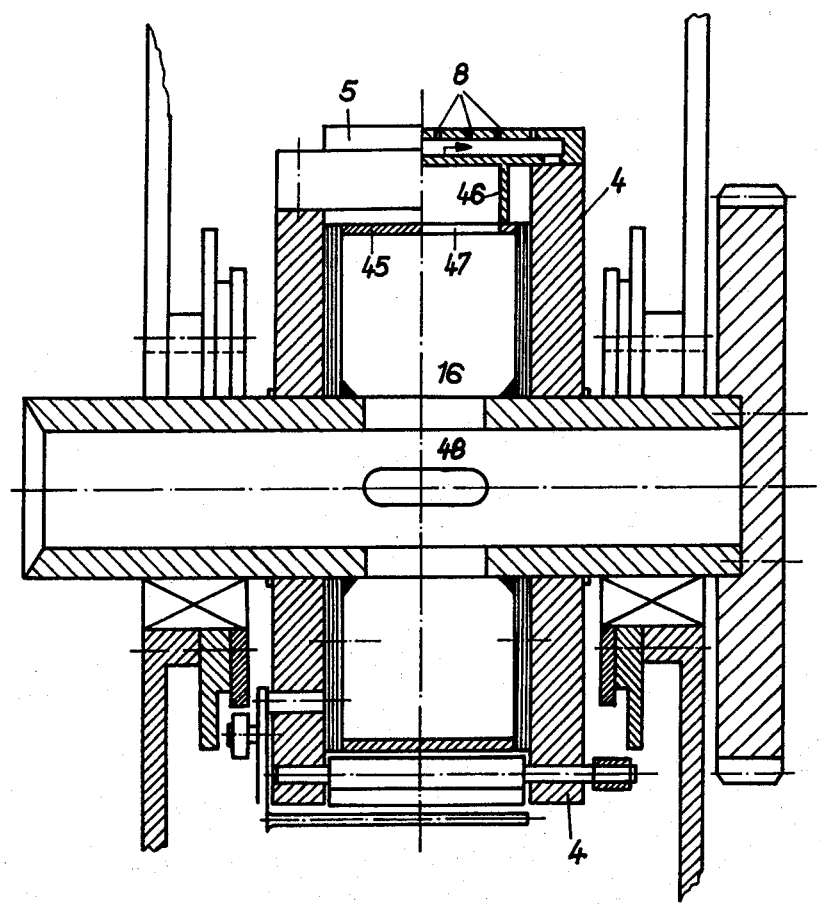
Figure 5:
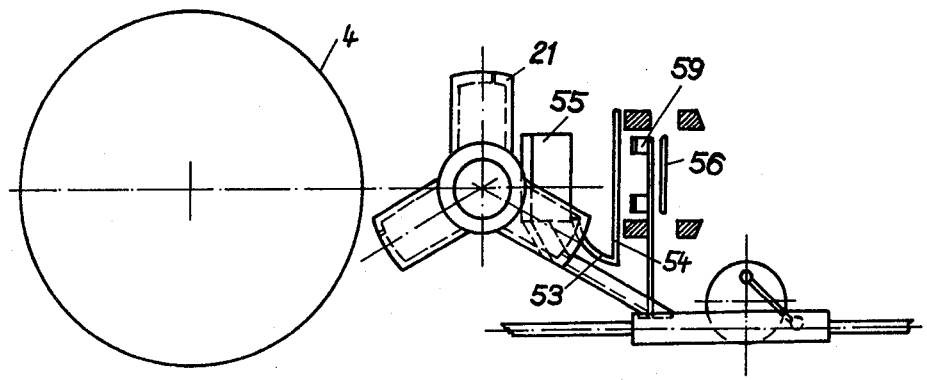
Figure 6:
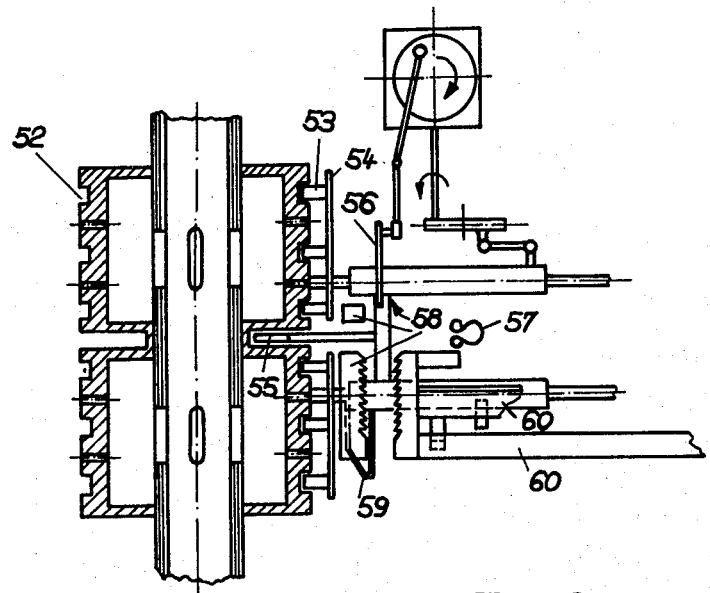
Figure 7:
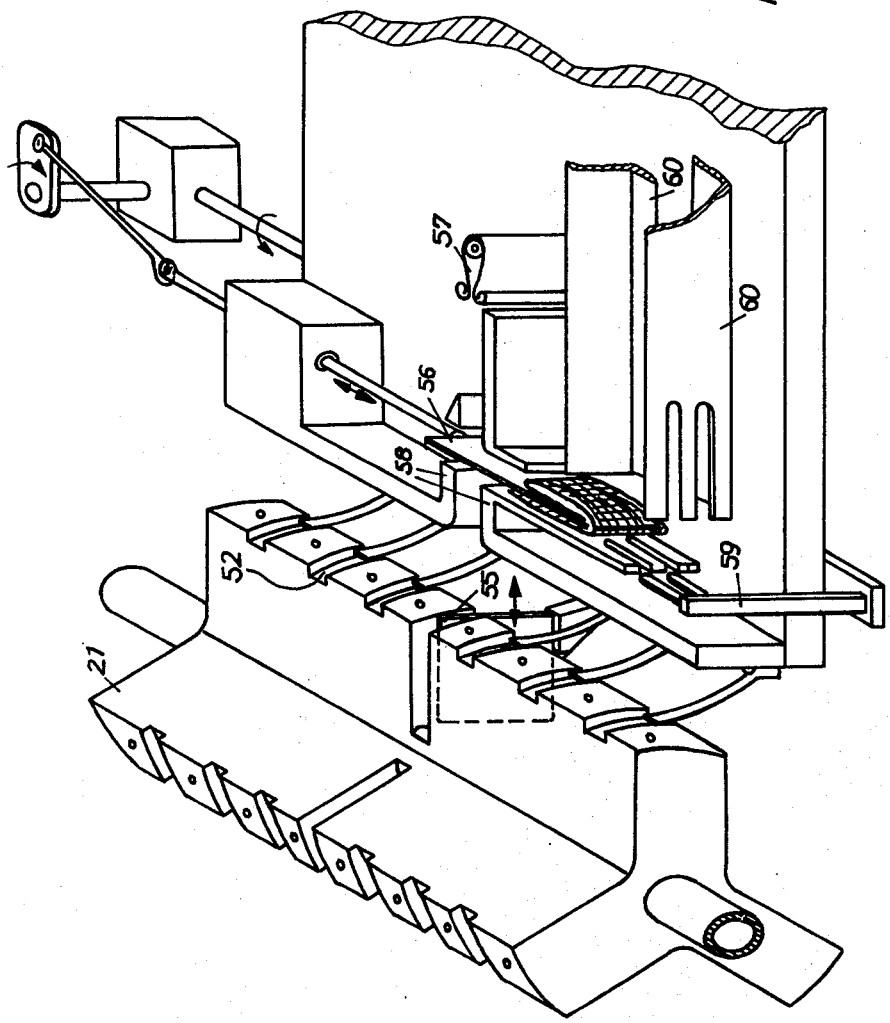
Figure 8:
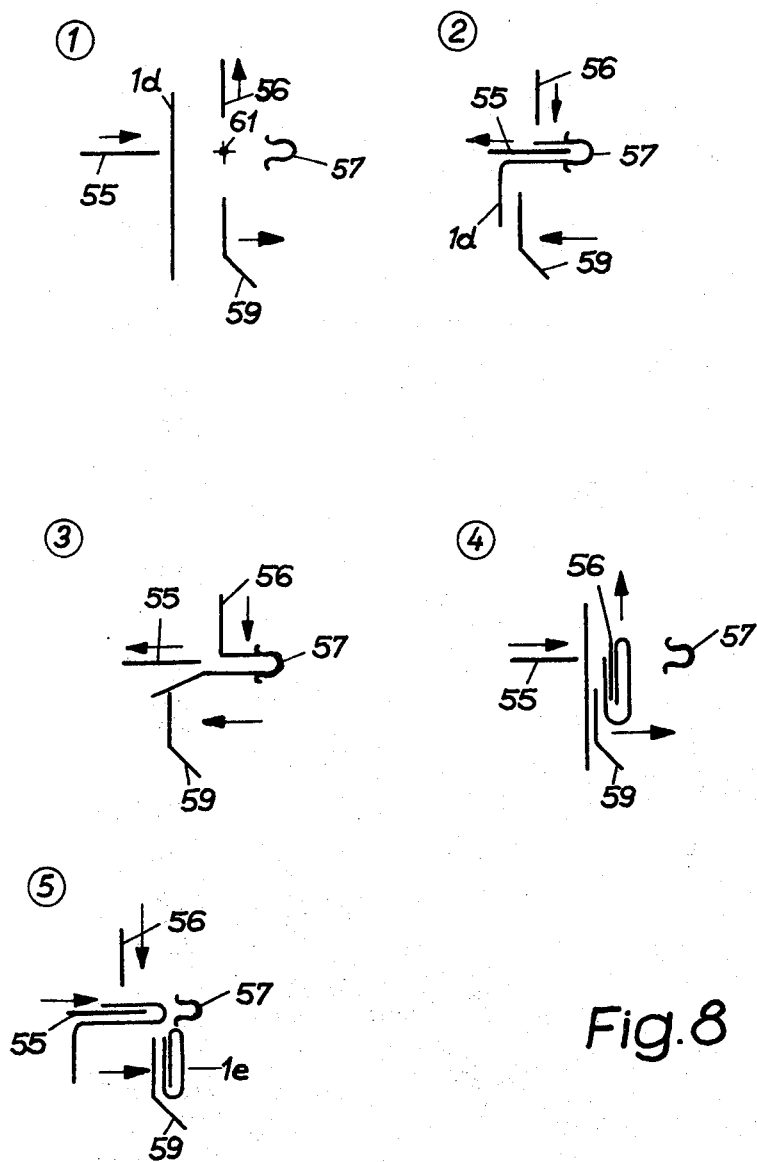
Figure 9:
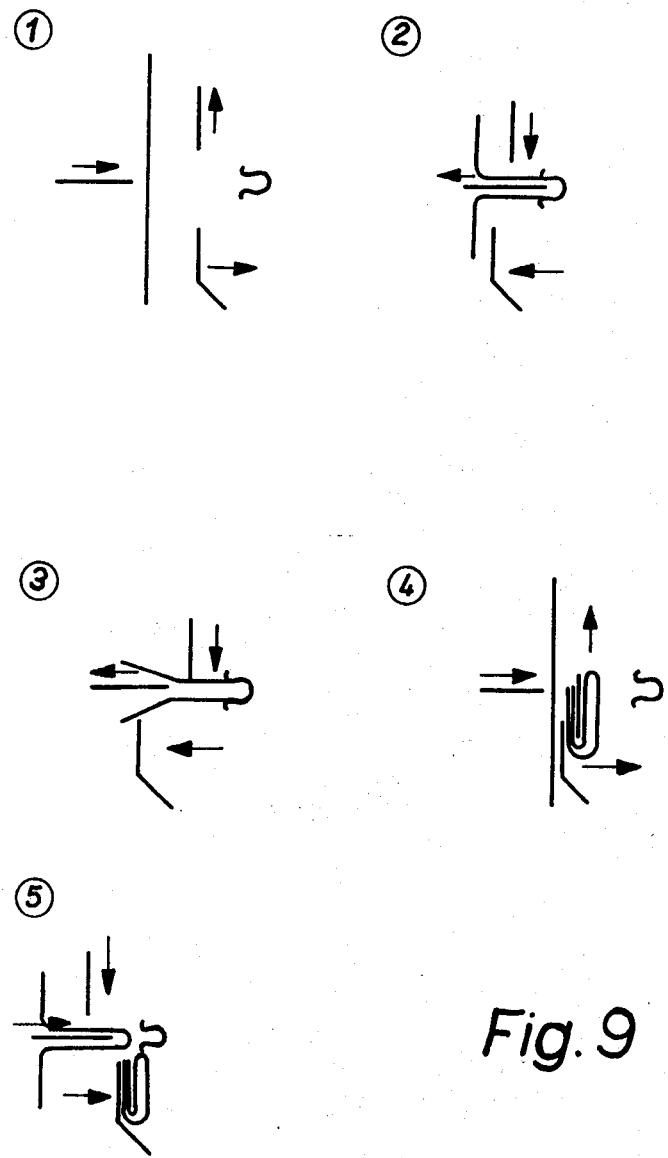
Figure 10:
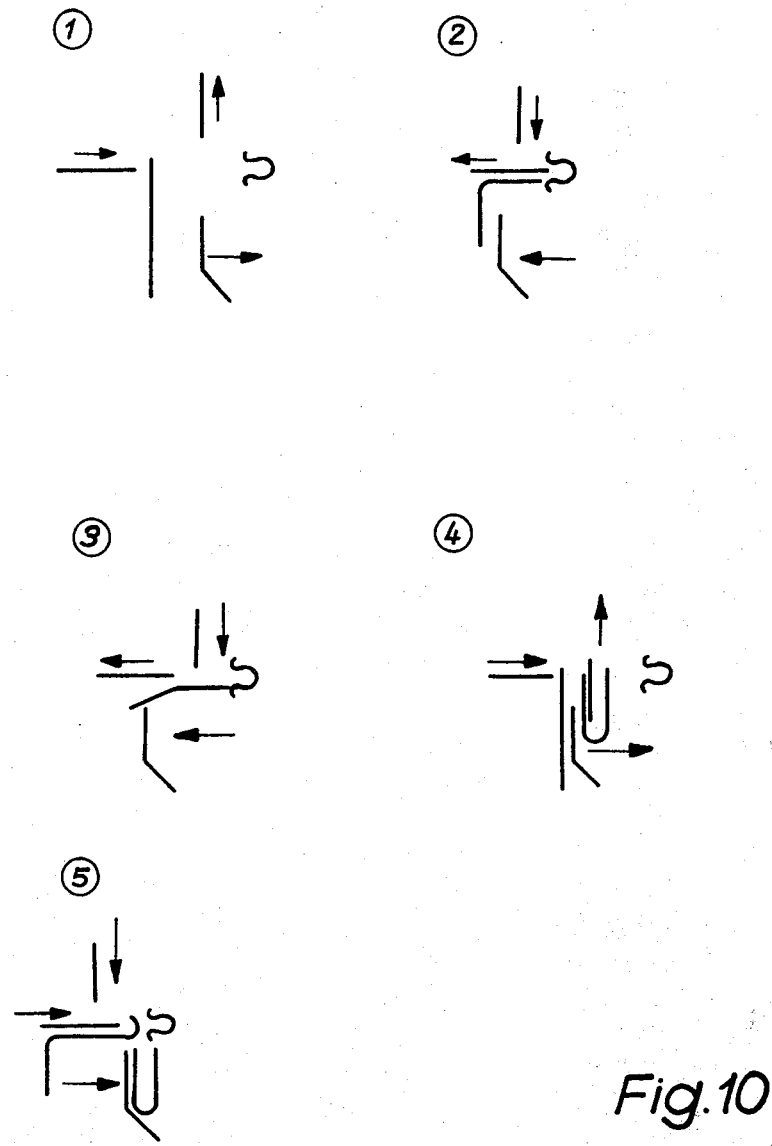

The invention will be explained in greater detail hereafter in connection with several embodiments of the invention and with reference to the accompanying drawings, in which:

FIG. 1 is a cross-section through the apparatus according to the invention.
FIG. 2 is a longitudinal section through the drum.
FIG. 3 the cross-section through the drum.
FIG. 4 shows the cutter plate.
FIG. 5 is a side-view of the apparatus according to the invention.
FIG. 6 is a longitudinal section through the longitudinal folding device.
FIG. 7 shows the longitudinal folding device in a perspective view with a diagonal section.
FIG. 8 shows diagrammatically the folding process for a U-fold.
FIG. 9 shows diagrammatically a VV-fold, and
FIG. 10 shows a V-fold.

The rolled muslin strip is fed to the drum 4 with its longitudinal edges folded over. On the drum 4 the muslin strip is severed between the cutters 5 having upper edges disposed radially outwardly of the drum and being set at the circumference and a counterpiece 6a or 6b mounted independently of the drum. It will be seen from FIG. 1 that a plurality of cutters 5 are distributed over the suction roll. The drum jacket has suction strips or rails 7 provided with bores ending in rows of opening 8 which are set with their extensions 46 on a tube 45 set into the drum 4, the extensions 46 defining fluid passageways. The tube 45 has slots 47 which correspond with the extensions 46 of the suction strips or rails 7. By means of a blower the air is sucked from the suction rails into tube 45 and from there through slots 48 in the drum shaft 16. It will of course be apparent from the drawing (see for instance FIG. 1) that the multiple suction strips 7 are spaced from each other to provide interstices therebetween about the periphery of the drum, and that the cutters 5 are disposed in certain of these interstices. It will be also apparent from the drawing (FIGS. 1 and 2) that the extensions 46 are hollow and that they extend radially inwardly from the suction strips proper. Likewise, it will be apparent from the drawing (FIG. 1) that each suction strip has one extension associated therewith. Finally, it will be apparent that tube 45 is disposed radially inwardly of the extensions 46.

According to a first embodiment of the invention the counterpiece 6a is a cylinder which is mounted at the periphery of drum 4 (FIG. 3) in order to obtain a complete and clean cut of the muslin strip.

In a further embodiment of the counterpiece 6b an elastic cutter plate 6b is clamped in at one side and which bears against the cutter 5 when the latter rotates away below the cutter plate, i.e., the cutter plate 6b will bend under the action of the cutter 5 so that the cutter 5 can pass by the elastic cutter plate 6b. The cutter plate 6b will thereafter spring back to recover its original shape shown in FIG. 4. In this manner the muslin strip is severed between the cutter 5 and the elastic cutter plate 6b (FIG. 4). The cutting effect is further improved when the cutter plate projects inwardly beyond the cutter towards the drum axis, i.e. the cutting edge of cutter plate 6 is mounted closer to the drum axis than the upper edges of the cutters 5 fixed to the drum.

In order to prevent the sudden rise of the cutter pressure and thus reduce the stress on the drum bearing, the cutter and the counterpiece, the cutter plate 6 is arranged at an incline to the tangent of the drum as will be clearly seen in FIG. 4. Such a mutual disposition of the cutter and cutter plate may also be reversed.

The cut muslin strip which is cross-folded in a known manner, i.e., which is folded on the drum along a first folding line parallel to the drum axis, is fed to the longitudinal folding device disposed adjacent the drum. In this process the compresses are received by a star-shaped collector unit device or 21 which has the same circumferential speed as drum 4. The collector unit 21 is connected to its own suction line and collects with each of its arms a compress from the drum 4. The number of the arms depends essentially on the length dimension of the compresses when on of the drum, the "length" dimension being regarded as that which runs transverse to the axis of the drum, as this must be equal to the distance between two successive arms measured at the circumference of the collector unit. Each compress is held on the collector surface at the free end of an arm of the collector unit by the air sucked through the collector unit until it is received by the folding device 54. The collector unit 21 is provided with grooves 52 at the collector surfaces in the circumferential direction. A rake 53 reaches into the collector unit 21. The rake is fixed at the face plate of the folding device 54 and collects the compresses. They slide along the collector rate 53 against the face-plate of the folding device 54. A folding plate 55 which is arranged normal to the rotary axis of the collector unit 21 and reaches into a circumferential groove thereof is moved in a folding trajectory. This trajectory is developed between two folding fingers 58 mounted at the face plate of the folding device 54 and presents at its end a clamping device 57 consisting of a spring. Between the folding fingers 58 and the clamping device 57 a second folding plate 56 is disposed parallel to the rotary axis of the collector unit 21, whose folding track leads at one end into a U-shaped canal 60 (FIG. 7).

When a compress has arrived at the rake 53 the folding plate 55 is already in its forward run and pushes the compress between the folding fingers 58 up to the reversing point. There the compress is held by a clamping device 57 so that it cannot be pulled back either by the folding plate 55 nor can it collapse which could happen particularly with a thin muslin fabric.

During the return travel of the folding plate 55 the folding plate 56 is in its forward travel. The stacking finger 59 moves at the same rhythm as the plate 55 and it stacks the completely folded compresses in a U-shaped canal 60.

In FIGS. 8 through 10 the movement of the two folding plates 55, 56 for obtaining a particular fold is shown diagrammatically. In the U-fold illustrated in FIG. 8 the compress is disposed in the collector rake in such a way that the folding plate 55 strikes the compress at the end of the first third of the compress length. As can be seen from FIGS. 9 and 10 the type of folding of the compress depends on its position to the folding plate 55. In the VV-fold the compress lies with its center portion and in the V-fold it lies with one end at the folding track of the folding plate 55.

This varying arrangement of the compresses is obtained according to an embodiment of the invention by the sliding movement of the longitudinal folding device parallel to drum 4. The collector unit necessary for this is wider than the compress and collects from the drum the compresses for the type of fold set in each case by the slideable adjustment.

In a further embodiment of the invention the collector device is only as wide as the compresses to be collected from the drum. In this regard, the "width" is regarded as the dimension parallel to the axis of the drum. The sliding adjustment of the folding plate 55 relative to the compresses is obtained by the sliding movement of the folding device 54 parallel to the rotary axis of the collector unit.

The folding plates 55, 56 are rigidly coupled with the star-shaped collector unit 21, so that the speed of the working rhythm depends on the number of rotations and the distances between the arms of the collector unit 21. That is, the device is controlled such that the speed of the working stroke depends on the number of rotations and the number of arms of the collector device 21, and the stacking plate 55 moves in the same rhythm as the stacking finger 59. The folding plates 55, 56 and the stacking finger 59 are regulated by the collector device 21 via an angle drive and via crank gears as shown in FIG. 2.

The stacking device can consist of a frame which is disposed at the end of the folding track of the folding plate 56, opposite which a frame is mounted in canal 60. Both frames can be provided with teeth which prevent that the folding plate can pull back the compress or that the compress collapses in itself, particularly in the case of very thin compress fabrics (FIG. 6).

What is claimed is:

1. Apparatus for producing compresses to cover wounds made from muslin strips having folded over edges, comprising: a rotary drum on which a muslin strip is cut and folded, a folding device mounted adjacent the drum, for effecting additional folding of the compresses which have been folded on the drum, the drum being in the form of a suction roll with cutters distributed over its circumference, said drum including a plurality of suction openings disposed in rows about the periphery of the drum, the cutters being disposed between the rows of suction openings, the drum including a plurality of fluid passageways which extend radially inwardly from the openings, a tube in the drum disposed radially inwardly of the passageways, the passageways being in fluid communication with the tube, the tube being connected to a suction pipe; a counterpiece which cooperates with the cutters, the counterpiece being mounted independently of the drum; the compresses which are folded on the drum having a length dimension, which length dimension runs transverse to the axis of the drum when the compress is on the drum in its folded condition; the circumference of the rotary drum moving at a certain circumferential speed during rotation of the drum, the folding device having a collector device which rotates about an axis parallel to the drum axis at the same circumferential speed as the drum itself, means for transferring compresses from the drum to the collector device and for holding the compresses on the collector device, said collector device having at least two radially extending arms which have radially outer free ends describing an outer circumference of the collector device, the distance between the arms of the collector device measured at the outer circumference of the collector device corresponding to the length dimension of the compresses folded on the drum, the collector device having slots in the arms thereof which are aligned in a plane substantially normal to the axis of the collector device, said slots being sized to receive a movable folding plate, and means to reciprocate said folding plate in a direction normal to the axis of said collecting device toward and into cooperative engagement with folding fingers which act to grasp a compress and fold respective halves thereof together.

2. Apparatus according to claim 1 wherein the rotary drum includes suction strips about its periphery, the suction openings being disposed in the suction strips, the suction strips having associated therewith hollow extensions which define said fluid passageways; wherein the tube has longitudinal slots distributed over its circumference and wherein the extensions of the suction strips are set over and in registry with the slots in a gas-tight arrangement on the tube.

3. Apparatus according to claim 1 wherein the counterpiece is a cylinder which is disposed tangentially to the drum axis.

4. Apparatus according to claim 3 wherein the counterpiece is a cylinder mounted parallel to the drum axis.

5. Apparatus according to claim 1 wherein the counterpiece is a cutting plate which is mounted non-slideably.

6. Apparatus according to claim 5 wherein the cutting plate is elastic.

7. Apparatus according to claim 6 wherein the cutting plate is mounted at an incline with respect to the tangent of the drum.

8. Apparatus according to claim 5 wherein the cutting plate includes a cutting edge and the cutters each have upper edges disposed radially outwardly of the drum for effecting cutting, the cutting edge of the cutting plate being mounted closer to the drum axis than the upper edges of the cutters fixed to the drum.

9. Apparatus according to claim 1, wherein said collector device has three radially extending arms, so that the collector device has a star-shaped configuration.

10. Apparatus according to claim 1, wherein the folding of compresses on the drum is along first folding lines which are parallel to the drum axis and wherein the additional folding effected by the folding device is along additional folding lines which are transverse to the first folding lines.

11. Apparatus according to claim 1, wherein the folding device also has a collector rake for collecting the compresses from the collector device and an additional folding plate disposed for sliding movement parallel to the axis of the collector device.

12. Apparatus according to claim 11 wherein the collector device has grooves for receiving the fingers of the collector rake.

13. Apparatus according to claim 12 wherein the collector device has a hollow interior and is connected to an air suction line and wherein the arms include collector surfaces and bores extending between the collector surfaces and the hollow interior.

14. Apparatus according to claim 13 wherein the folding device is mounted in slideable relationship relative to the drum and wherein the compresses folded on the drum have a width dimension which runs parallel to the axis of the drum when the compress is on the drum and wherein each arm of the collector device has a collector surface at its free end, the collector surface running parallel to the axis of rotation of the collector device, the axial dimension of the collector surface for the compresses being larger than the width dimension of the compresses which are collected from the drum.

15. Apparatus according to claim 14 wherein, between the folding fingers, two folding tracks are mounted which are disposed at right angles to each other, the folding plates being slideable in the folding tracks, one of the folding tracks being normal to the rotary axis of the collector device, the one folding track leading into a clamping device while at the end of the other folding track a stacking finger is mounted which stacks the completely folded compresses in a canal disposed perpendicularly thereto.

16. Apparatus according to claim 15 wherein the other folding track is parallel to the axis of the collector device and one end of the other folding track and the oppositely disposed end of the canal is designed as a frame into which reaches the stacking finger.

17. Apparatus according to claim 16 wherein the frame is provided with teeth mounted parallel to the other folding plate.

18. Apparatus according to claim 15 wherein the folding plates and the stacking finger are coupled with the collector device.

19. Apparatus according to claim 18 wherein the one folding plate which is normal to the rotary axis of the collector device is mounted in the center of the collector device.

20. Apparatus according to claim 19 wherein the one folding track which is normal to the axis of the collector device is slideable parallel to this axis.

21. Apparatus according to claim 18 wherein the folding plates and the stacking finger are regulated by the collector device via an angle drive and via crank gears.

22. Apparatus for producing compresses to cover wounds made from muslin strips having folded over edges, comprising: a rotary drum on which a muslin strip is cut and folded, a folding device mounted adjacent the drum, for effecting additional folding of the compresses which have been folded on the drum, the drum being in the form of a suction roll with cutters distributed over its circumference, said drum including a plurality of suction openings disposed in rows about the periphery of the drum, the cutters being disposed between the rows of suction openings, the drum including a plurality of fluid passageways which extend radially inwardly from the openings, a tube in the drum disposed radially inwardly of the passageways, the passageways being in fluid communication with the tube, the tube being connected to a suction pipe; a counterpiece which cooperates with the cutters, the counterpiece being mounted independently of the drum; the compresses which are folded on the drum having a length dimension, which length dimension runs transverse to the axis of the drum when the compress is on the drum in its folded condition; the circumference of the rotary drum moving at a certain circumferential speed during rotation of the drum, the folding device having a collector device which rotates about an axis parallel to the drum axis at the same circumferential speed as the drum itself, means for transferring compresses from the drum to the collector device and for holding the compresses on the collector device, said collector device having at least two radially extending arms which have radially outer free ends describing an outer circumference of the collector device, the distance between the arms of the collector device measured at the outer circumference of the collector device corresponding to the length dimension of the compresses folded on the drum, the collector device having slots in the arms thereof which are aligned in a plane substantially normal to the axis of the collector device, said slots being sized to receive a first movable folding plate, and means to reciprocate said first folding plate in a direction normal to the axis of said collecting device toward and into cooperative engagement with folding fingers which act to grasp a compress and fold respective halves thereof together, the folding device also having a collector rake for collecting the compresses from the collector device and a second folding plate disposed for sliding movement parallel to the axis of the collector device.

* * * * *